United States Patent [19]

Swearingen

[11] 4,442,704
[45] Apr. 17, 1984

[54] VISCOSITY METER

[76] Inventor: Judson S. Swearingen, 27403 Pacific Coast Hwy., Malibu, Calif. 90265

[21] Appl. No.: 397,096

[22] Filed: Jul. 12, 1982

[51] Int. Cl.$^3$ .......................................... G01N 11/08
[52] U.S. Cl. .................................................. 73/55
[58] Field of Search ................................ 73/55, 56, 64

[56] References Cited

U.S. PATENT DOCUMENTS

| 3,375,704 | 4/1968 | Thompson, Jr. et al. | 73/55 |
| 3,548,638 | 12/1970 | Uchida et al. | 73/55 |
| 3,869,922 | 3/1975 | Frajans et al. | 73/438 |
| 3,930,402 | 1/1976 | Detmar et al. | 73/55 |
| 3,981,202 | 9/1976 | Spangle | 73/438 |
| 4,165,632 | 8/1979 | Webber et al. | 73/55 |

FOREIGN PATENT DOCUMENTS

| 746340 | 3/1956 | United Kingdom | 73/55 |
| 389440 | 11/1973 | U.S.S.R. | 73/55 |

Primary Examiner—Gerald Goldberg
Assistant Examiner—Joseph W. Roskos
Attorney, Agent, or Firm—Lyon & Lyon

[57] ABSTRACT

A meter for continuously monitoring the viscosity of lubricating fluids. A fluid conduit extends across the element or bearing being lubricated to employ the differential pressure of the lubricant across that element. The fluid conduit includes an orifice in series with a capillary. The pressure differential across the capillary is then measured to provide an indication of viscosity. A shunt capillary controlled by a differential pressure relief valve is positioned parallel to the main capillary to reduce the sensitivity of the meter in areas of high viscosity. Protection against significantly heating or cooling the viscosity of the fluid provided to the meter is accomplished by placing the shunt capillary or a jacket of lubricating fluid about the main capillary.

7 Claims, 3 Drawing Figures

VISCOSITY METER

BACKGROUND OF THE INVENTION

The present invention is directed to viscosity meters and particularly to the continuous monitoring type useful in monitoring lubricating fluids.

With the widespread use of pressurized lubricating systems for bearings and the like, need for the continuous accurate monitoring of the condition of the lubricant has long been recognized. A variety of conditions may affect the efficiency of a lubricant which in turn can lead to disastrous consequences if not immediately corrected. For example, lubricant viscosity can be greatly affected by the environment in which the lubricant is used. In many conventional lubricants, the buildup of heat in equipment and specifically in the lubricant itself can cause a substantial lowering of its viscosity. Contamination can also affect the viscosity of the lubricant particularly if a large amount of contaminant is introduced into the lubricating system. Higher viscosities can result from selective vaporization of lubricants while chemical effects can bring about change in either direction. Thus, a wide range of conditions can affect the operative viscosity of a lubricant as it is being used.

The effects of changes in lubricant viscosity on the operation of bearings and the like can be very detrimental to the lubricant's performance and result in expensive and disruptive mechanical failure. This is particularly true with abnormally low lubricant viscosities. With decreased viscosity, the mechanism in which the lubricant is being employed may be unable to supply lubricant fast enough to the bearing surfaces to insure proper lubricating film. A decrease in oil film resonant frequencies can also result in high bearing wear; thus, regardless of the cause of the viscosity change, variations in lubricant viscosity can have a substantial adverse effect on bearing and component life.

Another factor directly effecting any lubricant performance is the pressure at which the lubricant is supplied to the bearing surfaces. As higher pressures are employed, the lubricant is better able to move into otherwise lubricant-starved areas, renew itself promptly enough to remain cool in high load areas and produce higher oil film resonant frequencies in the lubricated mechanisms. Thus, the performance of abnormally low viscosity lubricant can be improved with added pressure.

In the normal use of lubricants, a wide range of viscosity may be experienced. During cold start-up, viscosity may be quite large. During steady state running, the viscosity may approach a range very near a critical point. Consequently, a viscosity monitor may be required which can accurately distinguish between safe and unsafe conditions during steady state running and yet operate under conditions of great disparity in cold starting for example.

A variety of viscosity monitoring devices presently are available. These devices frequently require an input of power, external instrumentation or both. Furthermore, the required instrumentation is often expensive because of the need to provide high resolution as well as a broad range to insure accuracy in determining damaging lubricant conditions.

One common form of viscosity meter employs a capillary tube across which pressure is measured. Examples of such viscosity meter devices are illustrated in Thompson, Jr., et al., U.S. Pat. No. 3,375,704, Uchida et al., U.S. Pat. No. 3,548,638, Detmar et al, U.S. Pat. No. 3,930,402, and Webber, et al., U.S. Pat. No. 4,165,632. The Thompson, Jr., et al. patent also makes reference to another type of viscosity meter device which employs a pressure drop across an orifice as the means for detecting changes in viscosity.

SUMMARY OF THE INVENTION

The present invention is directed to a viscosity meter which is designed to provide increased resolution in the lower portion of the viscosity range through which the selected fluid is expected to perform. To this end, an orifice and a main capillary are employed in series with an associated shunt capillary across the main capillary. A pressure meter is used to measure the pressure drop across the main capillary to reflect the variation in viscosity of the fluid passing therethrough. The capillaries may be arranged with the shunt capillary concentrically arranged about the main capillary to aid in the retention of heat in the fluid contained within the main capillary. In addition, a fluid jacket may be employed about the entire system, again to maintain the temperature of the fluid in the device.

To obtain increased sensitivity at the lower viscosities, the shunt system is opened at a predetermined pressure. By employing such a shunt system, the expected range of pressure responsive to an expected range of viscosity is reduced. In the lower viscosity range where greatest danger exists to the equipment, a high degree of pressure sensitivity can be maintained. In the more viscous range where readings are less critical and damage less likely, the pressure sensitivity is reduced by employment of the shunt capillary. Thus, the overall range of response required of a differential pressure meter is reduced. A more sensitive response in the ranges of greatest danger can therefore be obtained.

As the system employs low flow, differential pressure elements, the system is substantially passive in nature. That is to say, no outside power is required to run the system or operate on the fluid. The minimal power required is supplied by the pressure drop of the relatively small amount of fluid passing through the meter. Furthermore, each device can be tailored to the flow rate of the fluid through the associated mechanisms such that the effect on the ability of the fluid to perform as intended is negligible. Yet, a biased output can be achieved to enhance the resolution of the system in the critical ranges of viscosity.

Viscosity meters of the present invention are particularly suited for employment to protect bearings of rotating machinery requiring a continuous and constant source of pressurized lubricant. Such equipment can be continuously monitored without need for additional power or excessive diversion of lubricant. The consistency of the pressure across the lubricated port is advantageous for accurate viscosity readings. However, errors created by anomalous pressures tend to support rather than detract from the general value of the metering system, i.e., protection of the lubricated equipment. Abnormally high pressures bias the metering system to reflect higher than actual readings while abnormally low pressures do the opposite. This relationship advantageously corresponds to the influence of lubricant pressure on the effectiveness of the lubricant system. For example, abnormally low lubricating system pressures would register low viscosity readings in metering systems of the present invention reflecting a dangerous condition which could in fact exist even though viscosity may be normal. Thus, the metering systems of the present invention are able to accommodate and properly respond to a variety of critical conditions, pressure, temperature and viscosity.

Accordingly, it is an object of the present invention to provide an improved viscosity meter capable of continuously monitoring the effectiveness of a lubricating system at a lubricated component. To this end the viscosity of a lubricant is advantageously measured with enhanced sensitivity in a given range. The meter may further provide for substantial maintenance of temperature while monitoring viscosity levels. Other and further objects and advantages will appear hereinafter.

DETAILED DESCRIPTION OF THE PREFERRED EMBODIMENT

The devices of the present invention are designed, among other things, to offer a capability of continuous monitoring of viscosity in a fluid stream. These devices provide increased resolution at critical viscosity ranges and yet can provide wide ranges of metering. In realizing these functional results, a number of embodiments and variations may be employed to best suit each measurement requirement.

Figure 1:
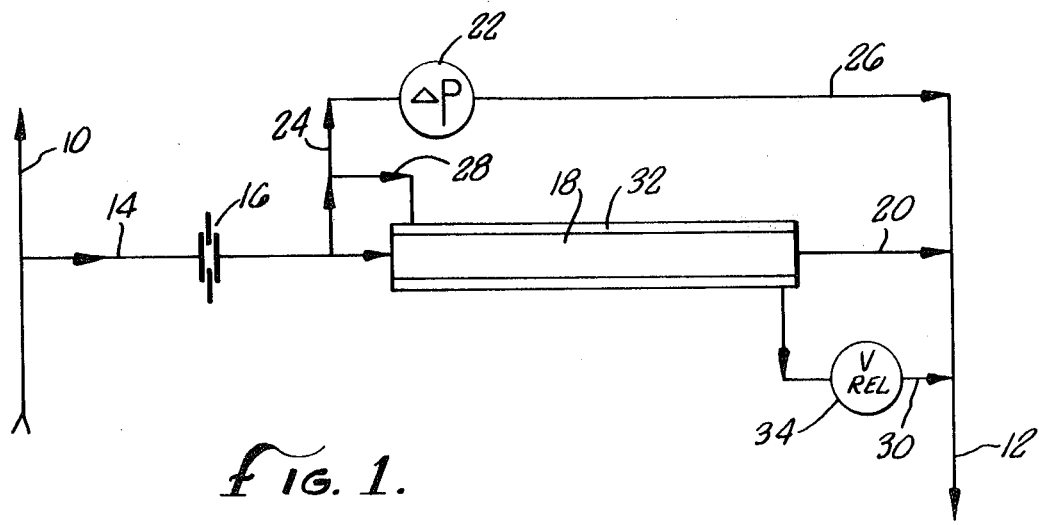
FIG. 1 is a schematic illustration of a viscosity monitor of the present invention.

FIG. 1 illustrates schematically a first system of the present invention. The actual construction of this device may be of any suitable, easily fabricated material such as synthetic resin or plastic. Such considerations as expected liquid temperatures and the solvent properties of the measured liquids must be taken into account when selecting suitable material.

A preferred use of the present invention is with pressurized lubricant systems for bearings or other lubricated components and a system is disclosed wherein the lubricant is fed through a passageway 10 immediately ahead of the bearings for which the lubricant is to be monitored. In this way, the lubricant has substantially the same temperature and viscosity through the meter as that entering the bearings. Furthermore, the lubricant system is generally understood to be maintained at a constant pressure through the passageway 10 as is generally true of high-speed turbomachinery. The return passageway 12 from the bearing is normally discharged to a lubricant reservoir. Thus, the meter of the present invention may most conveniently be mounted fluidically parallel to and physically adjacent the lubricated component.

The viscosity meter includes a fluid conduit including a main inlet 14, an orifice 16, a main capillary 18 and a main outlet 20. The orifice 16 and the main capillary 18 are so selected that in the range of approximately 90% of the pressure drop across the meter occurs at the orifice 16.

To measure the viscosity in terms of pressure drop, a differential pressure meter 22 is positioned to measure the pressure across the capillary 18. To do so, the higher pressure connection 24 to the fluid conduit is placed between the orifice 16 and the inlet to the capillary 18. The lower pressure connection 26 is conveniently coupled with the return conduit 12. For convenience, the differential pressure meter 22 may be calibrated directly in viscosity rather than in pressure quantities.

Arranged in parallel with the main capillary 18 is a shunt conduit. The shunt conduit includes a shunt inlet 28, a shunt outlet 30, a shunt capillary 32 and a differential pressure relief valve 34. The shunt inlet 28 communicates with the main fluid conduit downstream of the orifice 16 and upstream of the main capillary 18. The shunt outlet 30 communicates with the main fluid conduit which may be through the passageway 12 downstream of the main capillary 18.

The arrangement of the shunt conduit allows for flow parallel to the main capillary 18 as controlled by the differential pressure relief valve 34. The differential pressure relief valve 34 provides a means for controlling flow through the shunt conduit responsive to pressure across the main capillary. Naturally, the differential pressure relief valve 34 is selected such that it will open under pressures corresponding to viscosities well into the safe range for the protected bearing.

The shunt capillary 32 is also arranged concentrically about the main capillary 18. As lubricants are often subject to viscosity changes with temperature change, the concentric orientation of the shunt capillary 32 acts to insulate the main capillary 18 from the surrounding environment. This would be particularly true during early warm-up of the lubricant when viscosities are high. Furthermore, the system is made highly compact by this arrangement.

Figure 2:
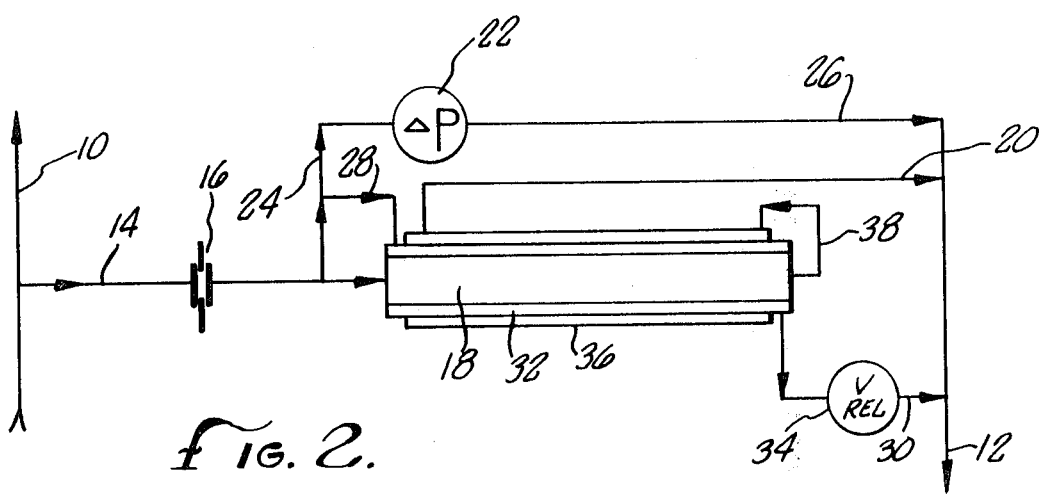
FIG. 2 is a schematic illustration of a second embodiment of the viscosity monitor of the present invention.

Looking next to FIG. 2, numbers corresponding to those employed with FIG. 1 are used for clarity of disclosure. In the embodiment of FIG. 2, a fluid jacket 36 is concentrically arranged around the main capillary 18 and also the shunt capillary 32. The fluid jacket draws flow directly from the main capillary 18 downstream of the capillary outlet through passage 38 and discharges through main outlet 20. The fluid jacket thereby receives continuous flow as it is in series with the main capillary 18. In this way, insulation about the main capillary 18 as well as the shunt capillary 32 is provided during all times of operation.

Through proper selection of the differential pressure relief valve 34, a system may be employed which gives high accuracy in a critical range and metering across a large range of viscosity. Viscosity in low viscosity ranges is measured by the differential pressure across the main capillary 18 by the differential pressure meter 22. This constitutes the total flow through the viscosity meter. A first sensitivity is thus realized. At higher viscosities, greater pressures are produced. At the higher pressures in the meter across the main capillary 18, the differential pressure relief valve 34 is opened and differential pressure across the two capillaries 18 and 32 increases at a slower rate with viscosity. Thus, reduced sensitivity in the range of high viscosity is achieved.

Figure 3:
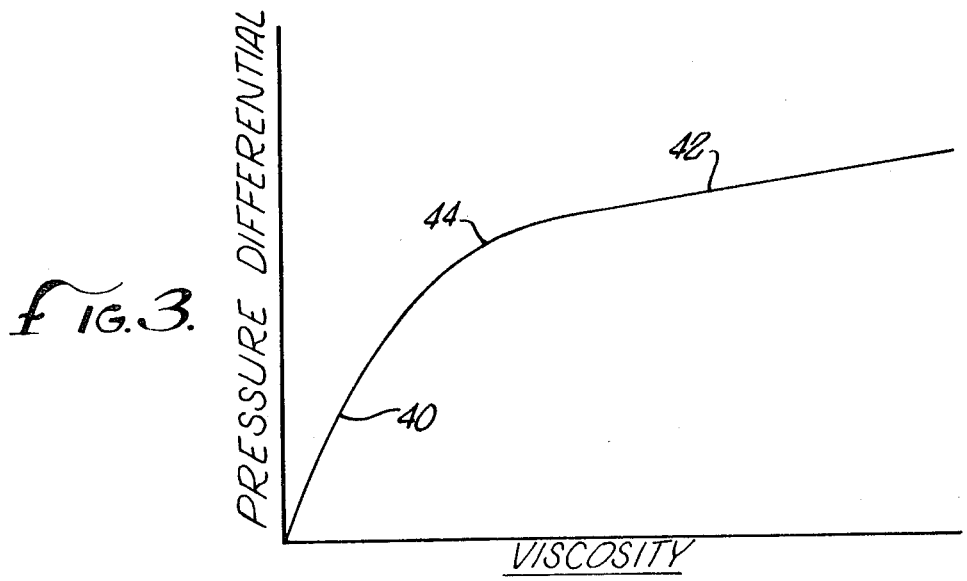
FIG. 3 is a typical viscosity-differential pressure response curve employing the meter of the present invention.

FIG. 3 illustrates the variation in sensitivity as measured by viscosity versus pressure differential across the meter 22. High sensitivity is achieved in the area of point 40 and low sensitivity in the area of point 42. A transition range in the area of point 44 is naturally experienced and is accommodated by calibration of the viscosity meter for each anticipated lubricant system pressure.

Thus, a simple, continuously operating viscosity meter is disclosed for measuring lubricants in a constant pressure lubricant system. Additionally, protection from environmental temperatures is also provided. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A viscosity meter comprising
 a fluid conduit including a main inlet, an orifice downstream of said main inlet, a main capillary downstream of said orifice, a main outlet downstream of said main capillary;
 a shunt conduit across said main capillary including a shunt inlet from said fluid conduit downstream of said orifice, a shunt outlet to said main outlet, a shunt capillary between said shunt inlet and said shunt outlet, and means for controlling flow through said shunt conduit responsive to pressure across said main capillary; and
 a differential pressure meter across said main capillary.

2. The viscosity meter of claim 1 wherein said means for controlling flow through said shunt conduit includes a differential pressure relief valve between said shunt inlet and said shunt outlet.

3. The viscosity meter of claim 1 wherein said shunt capillary is located concentrically about said main capillary.

4. The viscosity meter of claim 3 further including a fluid jacket about said shunt capillary, said fluid jacket being downstream of said main capillary and upstream of said outlet.

5. A viscosity meter for turbomachinery lubricant, comprising
 a constant source of pressurized lubricant;
 a fluid conduit including a main inlet in communication with said constant source, an orifice downstream of said main inlet, a main capillary downstream of said orifice, a main outlet downstream of said main capillary;
 a shunt conduit across said main capillary including a shunt inlet from said fluid conduit downstream of said orifice, a shunt outlet to said main outlet, a shunt capillary between said shunt inlet and said shunt outlet, and a differential pressure relief valve between said shunt inlet and said shunt outlet and
 a differential pressure meter across said main capillary.

6. The viscosity meter of claim 5 wherein said shunt capillary is located concentrically about said main capillary.

7. The viscosity meter of claim 6 further including a fluid jacket about said shunt capillary, said fluid jacket being downstream of said main capillary and upstream of said outlet.

* * * * *